(12) United States Patent
Brennan et al.

(10) Patent No.: US 7,737,096 B2
(45) Date of Patent: Jun. 15, 2010

(54) MILD ACYL ISETHIONATE TOILET BAR COMPOSITION

(75) Inventors: Michael Augustine Brennan, Sandy Hook, CT (US); Michael Massaro, Monroe, CT (US); Syed Husain Abbas, Seymour, CT (US); Yury Yarovoy, Monroe, CT (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 77 days.

(21) Appl. No.: 11/906,935

(22) Filed: Oct. 4, 2007

(65) Prior Publication Data
US 2008/0058237 A1 Mar. 6, 2008

Related U.S. Application Data

(63) Continuation-in-part of application No. 10/973,729, filed on Oct. 26, 2004, now abandoned.

(51) Int. Cl.
*A61K 7/00* (2006.01)

(52) U.S. Cl. .................. 510/141; 510/152; 510/153; 510/155

(58) Field of Classification Search .............. None
See application file for complete search history.

(56) References Cited

U.S. PATENT DOCUMENTS

| 2,894,912 | A | 7/1959 | Geitz |
|---|---|---|---|
| 3,376,229 | A | 4/1968 | Haass et al. |
| 4,007,125 | A | 2/1977 | Prince |
| 4,180,470 | A | 12/1979 | Cahn et al. |
| 4,663,070 | A | 5/1987 | Dobrovolny et al. |
| 4,812,253 | A | 3/1989 | Small et al. |
| 4,954,282 | A | 9/1990 | Rys et al. |
| 5,204,014 | A | 4/1993 | Redd et al. |
| 5,300,665 | A | 4/1994 | Tracy et al. |
| 5,372,571 | A | 12/1994 | Knelson et al. |
| 5,384,421 | A | 1/1995 | Day et al. |
| 5,441,671 | A | 8/1995 | Cheney et al. |
| 5,466,396 | A | 11/1995 | Madison et al. |
| 5,985,808 | A | 11/1999 | He et al. |
| 5,994,289 | A | 11/1999 | Nestler |
| 6,046,147 | A | 4/2000 | Cassady et al. |
| 6,121,216 | A | 9/2000 | Narath et al. |
| 6,248,703 | B1 | 6/2001 | Finucane et al. |
| 6,393,449 | B1 | 5/2002 | Blair et al. |
| 6,559,110 | B1 | 5/2003 | Lopes |
| 6,562,874 | B1 | 5/2003 | Ilardi et al. |

FOREIGN PATENT DOCUMENTS

| WO | 98/27193 | 6/1998 |
|---|---|---|
| WO | 01/42202 | 6/2001 |

*Primary Examiner*—Necholus Ogden, Jr.
(74) *Attorney, Agent, or Firm*—Alan A. Bornstein

(57) ABSTRACT

A mild toilet bar composition contains C8-C18 mono and diacyl isethionates in a specified ratio in a first preferred embodiment of the invention and a specified ratio of calcium and magnesium diacyl isethionates in a second preferred embodiment of the invention. Both toilet bars provide substantial lather, mild cleansing, low mush and wear rate levels during use.

19 Claims, 2 Drawing Sheets

MILD ACYL ISETHIONATE TOILET BAR COMPOSITION

This is a continuation-in-part of Ser. No. 10/973,729 filed on Oct. 26, 2004 now abandoned.

BACKGROUND OF THE INVENTION

1. Field of the Invention

This invention relates generally to cleansing bars, and more particularly to mild cleansing bars having substantial lather, low mush and wear rates.

2. The Related Art

Generally mild toilet bars are formulated with synthetic detergents (syndets) that replace soap to a large extent. Synthetic detergent or syndet toilet bars formulated with acyl isethionates or esterified fatty isethionates have found. considerable use as mild cleansing bars with excellent skin feel, lather, and slip properties but such bars may be difficult to process or have the potential to exhibit undesirable mush levels and high rates of wear unless formulated with substantial levels of structurants such as soap. It would be highly desirable to create a syndet bar based upon mild acyl isethionates that maintains its attractive skin feel properties, that is amenable to processing and that reduces the negative aspects of high mush levels and high rates of wear without the need for high levels of structurants, such as soap.

The use of toilet bars manufactured with DEFI (directly esterified fatty isethionate) technology particularly sodium isethionate, as a reactant with coco fatty acid has been disclosed in e.g. U.S. Pat. No. 2,894,912 issued to Geitz on Jul. 14, 1959. The use of "DEFI-like" mild surfactants through incorporation of alternative reactants to replace sodium isethionate (alkali metal isethionates or AIT) has been disclosed. U.S. Pat. No. 6,562,874 issued to Ilardi et. al., on May 13, 2003 teach the substitution of AIT with specific alcohols as well as fatty acid replacement with alternative carboxylic acids etc. and other formula modifications to enhance mildness. U.S. Pat. No. 3,376,229 issued to Haass and Lamberti on Apr. 2, 1968 disclose the use of AIT's to be used as firming agents. Tokosh and Cahn (U.S. Pat. No. 4,180,470 issued on Dec. 25, 1979) teach the use of alkoxy-hydroxy propane sulfonates as firming agents for bars.

The use of acyl isethionates with divalent metal counterions (e.g. Mg, Ca, etc.) has also been previously disclosed. For example, U.S. Pat. No. 5,994,289 issued to Nestler on Nov. 30, 1999 teaches the use of surfactant mixture containing acyl isethionates with mixed counterions, including ammonium, alkali metal and/or alkaline-earth metals. U.S. Pat. No. 6,559, 110 issued to Lopes on May 6, 2003 discloses a syndet bar comprising 0.1 to 95% by weight of at least one anionic surfactant such as acyl isethionate having a calcium or magnesium salt. U.S. Pat. No. 6,046,147 issued to Cassady et al. on Apr. 4, 2000 teaches a bar composition comprising 20 to 30% weight of acyl isethionate having a cation of an alkali earth metal and alkyl polyglycoside. U.S. Pat. No. 4,663,070 issued to Dobrovolny et al. on May 5, 1987 teaches a toilet bar comprising 2 to 45% acyl isethionate ester salt having a cation of ammonium, potassium, sodium, calcium or magnesium.

Unexpectedly it has been discovered that divalent metal isethionate(s) when used at a certain ratio and/or in combination with mono-valent C8-C18 isethionate(s) (such as e.g. cocoyl isethionate) form a complex with the DEFI reaction mixture as described below with a Krafft point comparable to that of mono-valent C8-C18 isethionate(s). Furthermore it was unexpectedly discovered that magnesium acyl isethionate forms a higher Krafft point complex then calcium acyl isethionate with the same Defi Reaction mixture.

When used in specific ratio ranges, these acyl isethionates provide a toilet bar that is mild, produces substantial lather, is more resistant to wear, and has less mush compared to prior art toilet bars composed of monovalent metal cocoyl isethionates alone. This is surprising since the art teaches that bars containing diacyl isethionates are generally less soluble than monoacyl isethionates and would therefore be expected to produce less lather during use when formulated into a toilet bar. Such toilet bars may also be processed within commercially acceptable parameters and with processing equipment typically used to manufacture toilet bars.

SUMMARY OF THE INVENTION

In one aspect of the invention is a toilet bar, including but not limited to the following:
(a) 0 to about 30% by wt. of a fatty acid soap; and
(b) about 15 to 75% by wt. of a blend of C8-C18 diacyl and monoacyl isethionates; wherein the ratio of the diacyl to monoacyl isethionates is in the range of about 1:100 to 1:1.

In another aspect of the invention is a toilet bar, including but not limited to the following:
(a) 0 to about 30% by wt. of a fatty acid soap; and
(b) about 20 to 70% by wt. of a blend of calcium and magnesium C8-C18 diacyl isethionates, wherein the ratio of calcium to magnesium diacyl isethionates is in the range of about 0.25 to 0.8.

DETAILED DESCRIPTION OF THE INVENTION

Figure 1:
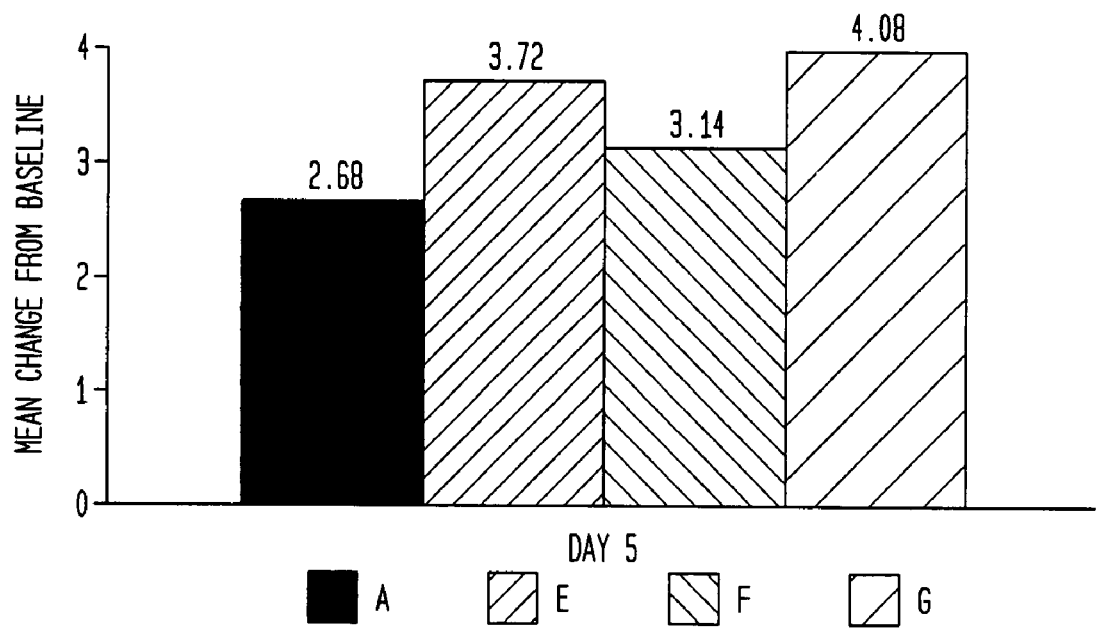
FIG. 1 is a bar chart of TEWL (transepidermal water loss) readings (mean change from baseline) of the toilet bars described in table 5.

In a first preferred embodiment of the invention is a toilet bar, including but not limited to the following:
(a) about 0 to 30% by wt. of a fatty acid soap; preferably where the upper limit is about 5, 10, 15, 20 or 25% by wt. and preferably where the fatty acid soap is C6 to C22 or more preferably C8 to C18;
(b) about 15 to 75% by wt. of a blend of C8-C18 diacyl and monoacyl isethionates; preferably where the blend of C8-C18 diacyl and monoacyl isethionates are present at least at about 30, 40, 50 or 56% by weight based on the toilet bar,
(c) wherein the ratio of the diacyl to monoacyl isethionates is in the range of about 0.04 to 0.5. The preferable upper limit of the ratio of diacyl to monoacyl isethionates is about 1:25, 1:20, or 1:15 and the preferred lower limit is about 1:3, 1:5, 1:8 or 1:10; and preferably wherein the bar has a yield stress value from about 300 Kpa to 650 KPa at 25° C. and 50% RH, as measured as described below. Alternatively the upper limit of yield stress value is preferably 240 KPa at 40° C. and 50% RH. In another embodiment, the yield stress value for the inventive bars is in the range of about 100 to about 300 KPa at 25° C. and 50% RH.

In the case where the inventive bar is intended to be extruded and stamped, the bar will preferably have an extensional stress rigidity of greater than about 100 Kpa at an extension rate of 0.03 sec-1 and 40° C., as measured by the extensional stress test described below. Preferably the extensional stress rigidity will be greater than about 150, 175, 200 or 215 Kpa measured at 40° C.

Advantageously there is about about 3% to 15% by weight of water in the bar (preferably less than 10%, 8%, 6% and 5%); and about 10 to 40% by wt. of a blend of C8 to C18 fatty acids, preferably C16 to C18, advantageously where the fatty acids are present in the concentration of at least 15, 20, 25 or 30% by wt.

Preferably there is about 0.1 to 15% by wt. of a blend of alkali and alkaline earth metal isethionate salts wherein the ratio of the alkaline earth to alkali metal isethionates is in the range of about 1:100 to 1:1. The preferable upper limit of the ratio of alkaline earth to alkali metal isethionates is about 1:30, 1:25, 1:20, or 1:15 and the preferred lower limit is about 1:3, 1:5, 1:8 or 1:10.

Advantageously the diacyl isethionate(s) counterion is/are selected from magnesium, calcium or a blend thereof and the monoacyl isethionate(s) counterion, in this case is/are selected from sodium, potassium or a blend thereof. The diacyl isethionate(s) counterion may also include other divalent cations in addition to magnesium and calcium such as zinc.

The monoacyl isethionate(s) counterion may also include other monovalent cations.

Preferably the inventive toilet bar contains 0 to about 20% by wt. of a fatty acid soap. The preferred amount of fatty acid soap can be at least about 1, 3, 4, 6, 8 or 10% by weight.

More preferably the inventive bar contains about 35 to 74% by wt. of C8-C18 monoacyl isethionates and about 0.1 to 35% by wt. of C8-C18 diacyl isethionates. The preferred upper level of monoacyl isethionate is at least about 40, 50, 55 or 65% by weight. The preferred upper level of diacyl isethionate is at least about 2, 4, 6 or 8% by weight.

Advantageously at least about 60, 70, 80, 90, or 95% of the total diacyl isethionate(s) present in the inventive bar is magnesium cocoyl isethionate and at least about 60, 70, 80, 90, or 95% of the total monoacyl isethionate(s) present is sodium cocoyl isethionate. Preferably an inventive bar capable of being extruded contains about 35 to 90% by wt. of the blend of C8-C18 alkali and alkaline earth metal acyl isethionates. The preferred upper level of the blend of C8-C18 alkali and alkaline earth metal acyl isethionates is at least about 40, 50, 60 or 75% by weight. More preferably the C8-C18 alkali and alkaline earth metal acyl isethionates are present in the extrudable bar in the range of about 40 to 50% by wt. By comparison, an inventive bar capable of being melt cast contains preferably about 30 or 25% by wt. or less of the blend of C8-C18 alkali and alkaline earth metal acyl isethionates.

Preferably the bar contains about 0.1 to 10% by wt. of sodium isethionate and about 0.1 to 10% by wt. of magnesium isethionate. The sodium isethionate may advantageously be as low as about 0.5, 1, 1.5, and 2% by wt. and may advantageously be as high as about 3, 4, 5, or 6% by weight. The magnesium isethionate may advantageously be as low as about 0.5, 1, 1.5, or 2% by wt. and may advantageously be as high as about 3, 4, 5, or 6% by weight. The calcium isethionate may advantageously be as low as about 0.5, 1, 1.5, or 2% by wt. and may advantageously be as high as about 3, 4, 5, or 6% by weight.

In a second preferred embodiment of the invention is a toilet bar, including but not limited to the following:
(a) 0 to about 30% by wt. of a fatty acid soap; and
(b) about 20 to 70% (more preferably about 30 to 60, most preferably about 45 to 55%) by wt. of a blend of calcium and magnesium C8-C18 diacyl isethionates; wherein the ratio of calcium to magnesium diacyl isethionates is in the range of about 0.25 to 0.8.

Advantageously, the bar has a yield stress value from about 120 KPa to 240 KPa at 40° C. and 50% RH. Preferably the toilet bar further includes one or more C8-C18 monoacyl isethionates; wherein the maximum ratio of mono to diacyl isethionates is about 0.5. More preferably the ratio of calcium to magnesium is in the range of about 0.4 and 0.8.

Preferably the toilet further includes about 0.1 to 15% by wt. of a blend of alkali and alkaline earth metal isethionate salts wherein the blend ratio of the alkaline earth to alkali metal isethionates is in the range of about 0.04 to 0.5. More preferably the bar contains about 0.1 to 10% by wt. of sodium isethionate and about 0.1 to 10% by wt. of magnesium isethionate.

Advantageously the fatty acid soaps in the inventive bar include a blend of C6 to C22 soaps, preferably C8 to C18 soaps. In a preferred embodiment the inventive bar further includes a non-soap anionic surfactant selected from C8 to C22 alkyl sulfate(s), C8 to C22 alkyl sulfosuccinate(s), C8 to C22 alkyl sulfonate(s); C8 to C22 fatty acid ester sulfonate(s), derivatives, and blends thereof in a range of 0.1 to about 15% by wt. as the total amount of non-soap anionic surfactants excluding isethionates. Preferably the total amount of non-soap anionic surfactant(s) excluding isethionates is at least about 2, 3, 4, or 5% by weight.

Preferably the bar further includes at least about 0.05% by wt. of one or more zinc or zirconium compounds or blends thereof, preferably their oxides, halides or soaps selected advantageously from zinc oxide, zirconium oxide, zinc chloride, zinc cocoate, blends thereof or the like. Preferably the zinc or zirconium compound(s) or a blend thereof is present up to about 5, 4, 3, 2, 1, 0.8, 0.5 or 0.2% by wt. in total amount based on the bar and preferably at up to about 0.15, 0.13, or 0.10% by wt.

Advantageously the amount of free water is less than about 15% by wt. in the inventive bar. Preferably the free water can be present up to maximum of about 10, 8, 6 or 5% by weight. Free water is herein defined as that quantity of water present in the bar that is able to solvate water-soluble materials. This ability is in contrast to that of bound water, such as the water of crystallization of unsolvated materials, other hydrate complexes and the like, whereby the bound water is unable to solvate water soluble materials to the same extent that free water can.

Preferably the inventive bar includes at least about 0.01% by wt. of a hydrophobic emollient. Preferably the hydrophobic emollient is selected from silicone oils, glyceride oils (such as jojoba, soybean, sunflower, olive, coconut and the like), mineral oils, and waxes (such as beeswax, carnauba, lanolin), and the like. More preferably the inventive bar contains at least about 5, 10, 15, 20, or 25% by wt. of a free fatty acid.

In a preferred embodiment, the Mush Factor of the inventive bar is in the range of about 0.99 to about 0.3. The Mush Factor is the ratio of mush value of inventive soap to control soap without alkaline earth acyl isethionate as measured with the mush technique described below. The preferred Mush Factor is less than about 0.9, 0.8, or more preferably less than about 0.7.

Surfactants:

Surfactants are an essential component of the inventive toilet bar. They are compounds that have hydrophobic and hydrophilic portions that act to reduce the surface tension of the aqueous solutions they are dissolved in. Useful surfactants in addition to the required mono and diacyl isethionates can include soap(s), and non-soap anionic, nonionic, amphoteric, and cationic surfactant(s), and blends thereof.

Anionic Surfactants:

Mono and Diacyl Isethionates

In one embodiment of the invention, the inventive toilet bar contains both monoacyl and diacyl C8-C18 isethionate surfactants having the general formula:

$$R\ C\text{—}O(O)\text{—}CH_2\text{—}CH_2\text{—}SO_3M^+$$

or $$(R\ C\text{—}O(O)\text{—}CH_2\text{—}CH_2\text{—}SO_3)_2M^{++}$$

wherein R is an alkyl group having 8 to 18 carbons, and M is a mono or divalent cation such as, for example, sodium, potassium, ammonium, calcium and magnesium or other mono and divalent cations. Preferably the isethionates have an average iodine value of less than 20. In a second embodiment of the invention, the bar contains both magnesium and calcium diacyl isethionates and optionally monoacyl and other diacyl isethionates.

Preferably the mono and diacyl isethionates used in the present invention are produced by a "DEFI" reaction where a mixture of a C8-C18, preferably C10 to C15 fatty acids (e.g., lauric and coconut acid) reacts with alkali metal isethionate as follows:

$$R\ C\text{—}O(OH)+HO\text{—}CH_2\text{—}CH_2\text{—}SO_3^-M^{++} \rightarrow R\ C\text{—}O(O)\text{—}CH_2\text{—}CH_2\text{—}SO_3M \text{ (plus residual starting materials)}$$

or $$R\ C\text{—}O(OH)+(HO\text{—}CH_2\text{—}CH_2\text{—}SO_3)_2^{--}M^{++} \rightarrow (R\ C\text{—}O(O)\text{—}CH_2\text{—}CH_2\text{—}SO_3)_2M \text{ (plus residual starting materials)}$$

The reaction is advantageously conducted at a stoichiometric ratio of about 1 to 1 to 2 to 1 fatty acid to isethionate using 0.01% to 1%, preferably 0.1% to 0.4% of total reactants by weight of a catalyst (e.g., zinc oxide, zirconium oxide, zinc isethionate or any Lewis acid including sulfuric acid, p-toluene sulfonic acid, sodium bisulfite etc.) at a temperature of about 150° C. to 250° C., preferably about 200° C. to 250° C. for about 1 to 3 hours. It is often advantageous to use a relatively small amount of the final product (produced earlier) as an emulsifying agent for the reaction mixture to help speed up the reaction. The components of the reaction may be added in any order and, although yields may be better reacting one agent before another, any order of addition is contemplated.

Other Anionic Surfactants

The inventive bar may contain one or more non-soap anionic detergent(s) (syndets) other than acyl isethionates. Preferably the syndet(s) have a zein value of 50 or less with the first test method provided below or have a zein value of under 2.5% with the second test method provided below.

Advantageously such non-soap anionic detergent(s) or surfactant(s) may be used from about 15, 20 or 30% by wt. to about 40, 50 or 60% by wt.

The anionic detergent active which may be used may be aliphatic sulfonate(s), such as a primary alkane (e.g., $C_8$-$C_{22}$) sulfonate(s), primary alkane (e.g., $C_8$-$C_{22}$) disulfonate(s), $C_8$-$C_{22}$ alkene sulfonate(s), $C_8$-$C_{22}$ hydroxyalkane sulfonate(s) or alkyl glyceryl ether sulfonate(s) (AGS); or aromatic sulfonate(s) such as alkyl benzene sulfonate.

The anionic may also be alkyl sulfate(s) (e.g., $C_{12}$-$C_{18}$ alkyl sulfate) or alkyl ether sulfate (including alkyl glyceryl ether sulfates). Among the alkyl ether sulfate(s) are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinate(s) (including mono-and dialkyl, e.g., $C_6$-$C_{22}$ sulfosuccinate(s)); alkyl and acyl taurate(s), alkyl and acyl sarcosinate(s), sulfoacetate(s), $C_8$-$C_{22}$ alkyl phosphate(s) and phosphate(s), alkyl phosphate ester(s) and alkoxyl alkyl phosphate ester(s), acyl lactate(s), $C_8$-$C_{22}$ monoalkyl succinate(s) and maleate(s), sulphoacetate(s), and alkyl glucoside(s) and the like.

Sulfosuccinates may be monoalkyl sulfosuccinates having the formula:

$$R^4O_2CCH_2CH(SO_3M)CO_2M;\ \text{and}$$

amide-MEA sulfosuccinates of the formula;

$$R^4CONHCH_2CH_2O_2CCH_2CH(SO_3M)CO_2M$$

wherein $R^4$ ranges from $C_8$-$C_{22}$ alkyl and M is a solubilizing cation.

Sarcosinates are generally indicated by the formula:

$$R^1CON(CH_3)CH_2CO_2M,$$

wherein $R^1$ ranges from $C_8$-$C_{20}$ alkyl and M is a solubilizing cation.

Taurates are generally identified by formula:

$$R^2CONR^3CH_2CH_2SO_3M$$

wherein $R^2$ ranges from $C_8$-$C_{20}$ alkyl, $R^3$ may be H or $C_1$-$C_4$ alkyl and M is a solubilizing cation.

Fatty Acid Soap

The inventive toilet bar may include low levels of soap and preferably under 10% by wt. of soap. The term "soap" is used here in its popular sense, i.e., the alkali metal or alkanol ammonium salts of aliphatic alkane-or alkene monocarboxylic acids preferably having about 12 to 22. carbon atoms, more preferably about 12 to about 18 carbon atoms. They may be further described as alkali metal carboxylates of aliphatic hydrocarbons. Sodium, potassium, mono-, di-and tri-ethanol ammonium cations, or combinations thereof, are suitable for purposes of this invention. In general, sodium soaps are used in the compositions of this invention, but from about 1% to about 25% of the soap may be potassium soaps. The soaps may contain unsaturation in accordance with commercially acceptable standards. Excessive unsaturation is normally avoided to minimize color and odor issues. In a preferred embodiment of the invention the bars have a fatty acid to soap ratio greater than 2:1 in order to maintain a neutral pH (6.9 to 7.2) when the bar is contacted with water.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

Amphoteric Surfactants

One or more amphoteric surfactants may be used in this invention. Advantageously amphoteric surfactants may be used from about 1, 2 or 3% by wt. to about 5, 6 or 7% by wt. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1—[—C(O)—NH(CH_2)_n—]_m—N^+—(R^2)(R^3)X—Y$$

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —$CO_2$— or —$SO_3$—

Suitable amphoteric surfactants within the above general formula include simple betaines of formula:

$$R^1—N^+—(R^2)(R^3)CH_2CO_2^-$$

and amido betaines of formula:

$$R^1—CONH(CH_2)_n—N^+—(R^2)(R^3)CH_2CO_2^-$$

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

$$R^1—N^+—(R^2)(R^3)(CH_2)_3SO_3^-$$

or $$R^1—CONH(CH_2)_m—N^+—(R^2)(R^3)(CH_2)_3SO_3^-$$

where m is 2 or 3, or variants of these in which —$(CH_2)_3$ $SO_3^-$ is replaced by $$—CH_2C(OH)(H)CH_2SO_3^-$$

In these formulae $R^1$, $R^2$ and $R^3$ are as discussed previously.

Amphoacetates and diamphoacetates are also intended to be covered in the zwitterionic and/or amphoteric compounds which are used such as e.g., sodium lauroamphoacetate, sodium cocoamphoacetate, and blends thereof, and the like.

Nonionic Surfactants

One or more nonionic surfactants may also be used in toilet bar composition of the present invention. When present, nonionic surfactants may be used at levels as low as about 1, 2 or 3% by wt. and as high as about 10, 15 or 20% by wt.

The nonionics which may be used include in particularly the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Skin Conditioning Agents

An optional component in compositions according to the invention is a cationic skin feel agent or polymer, such as for example cationic celluloses or polyquarterium compounds.

Advantageously cationic skin feel agent(s) or polymer(s) are used from about 0.01, 0.1 or 0.2% by wt. to about 1, 1.5 or 2.0% by wt. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200, and quaternary ammonium compounds such as alkyldimethylammonium halogenides.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially Jaguar C13S. Other cationic skin feel agents known in the art may be used provided that they are compatible with the inventive formulation.

Other preferred cationic compounds that are useful in the present invention include amido quaternary ammonium compounds such as quaternary ammonium propionate and lactate salts, and quaternary ammonium hydrolyzates of silk or wheat protein, and the like. Many of these compounds can be obtained as the Mackine™ Amido Functional Amines, Mackalene™ Amido functional Tertiary Amine Salts, and Mackpro® cationic protein hydrolysates from the McIntyre Group Ltd. (University Park, Ill.).

In a preferred embodiment of the invention having a hydrolyzed protein conditioning agent, the average molecular weight of the hydrolyzed protein is preferably about 2500. Preferably 90% of the hydrolyzed protein is between a molecular weight of about 1500 to about 3500. In a preferred embodiment, MACKPRO™ WWP (i.e. wheat germ amido dimethylamine hydrolyzed wheat protein) is added at a concentration of 0.1% (as is) in the bar. This results in a MACK-PRO™ WWP "solids" of, 0.035% in the final bar formula for this embodiment.

Cationic Surfactants

One or more cationic surfactants may also be used in the inventive toilet bar composition. Advantageously cationic surfactants may be used from about 0.1, 0.5 or1.0% by wt. to about 1.5, 2.0 or 2.5% by wt.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar. 27, 1973; and "Surface Active Agents and Detergents" (Vol. I & II) by Schwartz, Perry & Berch, both of which are also incorporated into the subject application by reference.

In addition, the toilet bar of the invention may include 0 to 15% by wt. optional ingredients as follows: perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise preservatives such as dimethyloldimethylhydantoin (Glydant XL1000), parabens, sorbic acid etc., and the like. The compositions may also comprise coconut acyl mono-or diethanol amides as suds boosters, and strongly ionizing salts such as sodium chloride and sodium sulfate may also be used to advantage. Antioxidants such as, for example, butylated hydroxytoluene (BHT) and the like may be used advantageously in amounts of about 0.01% or higher if appropriate.

Skin conditioning agents such as emollients are advantageously used in the present invention. Hydrophilic emollients including humectants such as polyhydric alcohols, e.g. glycerin and propylene glycol, and the like; polyols such as the polyethylene glycols listed below, and the like and hydrophilic plant extracts may be used. Advantageously humectants may be used from about 0.01, 0.2 or 1.0% by wt. to about 3, 5 or 10% by wt. Humectants may also confer the ability for the bar to retain water.

| | |
|---|---|
| Polyox WSR-205 | PEG 14M, |
| Polyox WSR-N-60K | PEG 45M, or |
| Polyox WSR-N-750 | PEG 7M. |

Hydrophobic emollients may be used in the inventive toilet bar. Advantageously hydrophobic emollients may be used from about 5, 10 or 15% by wt. to about 20, 25, 30, 35, 40, 45% by wt. The term "emollient" is defined as a substance which softens or improves the elasticity, appearance, and youthfulness of the skin (stratum corneum) by increasing its water content, and keeps it soft by retarding the decrease of its water content.

Useful hydrophobic emollients include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic plant extracts;

(e) hydrocarbons such as liquid paraffin, petrolatum, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils; and (j) mixtures of any of the foregoing components, and the like.

Preferred hydrophobic emollient moisturizing agents are selected from fatty acids, di and triglyceride oils, mineral oils, petrolatum, and mixtures thereof; with fatty acids being most preferred.

Krafft Point

The Krafft point of a surfactant is defined as the temperature (or more precisely, the narrow temperature range) above which the solubility of a surfactant rises sharply. At this temperature the solubility of the surfactant becomes equal to the critical micelle concentration. It may be determined by locating the abrupt change in slope of a graph of the logarithm of the solubility against temperature or 1/T or can be rapidly estimated using the rapid estimation procedure described below. Preferably the DEFI reaction mixture used in the inventive bar has a Krafft point of greater than 30 degrees Celsius.

Exfoliants

The inventive toilet bar may contain particles that are greater than 50 microns in average diameter that help remove dry skin. Not being bound by theory, the degree of exfoliation depends on the size and morphology of the particles. Large and rough particles are usually very harsh and irritating. Very small particles may not serve as effective exfoliants. Such exfoliants used in the art include natural minerals such as silica, talc, calcite, pumice, tricalcium phosphate; seeds such as rice, apricot seeds, etc; crushed shells such as almond and walnut shells; oatmeal; polymers such as polyethylene and polypropylene beads, flower petals and leaves; microcrystalline wax beads; jojoba ester beads, and the like. These exfoliants come in a variety of particle sizes and morphology ranging from micron sized to a few mm. They also have a range of hardness. Some examples are given in table A below.

TABLE A

| Material | Hardness (Mohs) |
|---|---|
| Talc | 1 |
| Calcite | 3 |
| Pumice | 4-6 |
| Walnut Shells | 3-4 |
| Dolomite | 4 |
| Polyethylene | ~1 |

Optional Active Agents

Advantageously, active agents other than skin conditioning agents defined above may be added to the toilet bar. These active ingredients may be advantageously selected from bactericides, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; or mixtures thereof; and the like.

These active agents may be selected from water soluble active agents, oil soluble active agents, pharmaceutically-acceptable salts and mixtures thereof. The term "active agent" as used herein, means personal care actives which can be used to deliver a benefit to the skin and/or hair and which generally are not used to confer a skin conditioning benefit, such are delivered by emollients as defined above. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent(s) will vary with the specific active agent, the ability of the active to penetrate through the skin, the age, health condition, and skin condition of the user, and other like factors. Preferably the compositions of the present invention comprise from about 0.0001% to 50%, more preferably from about 0.05% to 25%, even more preferably about 0.1% to 10%, and most preferably about 0.1% % to 5%, by weight of the active agent component(s).

A wide variety of active agent ingredients are useful herein and include those selected from anti-acne actives, anti-wrinkle and anti-skin atrophy actives, skin barrier repair aids, cosmetic soothing aids, topical anesthetics, artificial tanning agents and accelerators, skin lightening actives, antimicrobial and antifungal actives, sunscreen actives, sebum stimulators, sebum inhibitors, anti-glycation actives and mixtures thereof and the like.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, mixtures thereof and the like.

Antimicrobial and antifungal actives can be effective to prevent the proliferation and growth of bacteria and fungi. Nonlimiting examples of antimicrobial and antifungal actives include b-lactam drugs, quinolone drugs, ciprofloxacin, norfloxacin, tetracycline, erythromycin, amikacin, 2,4,4'-trichloro-2'-hydroxy diphenyl ether, 3,4,4'-Trichlorocarbanilide (triclocarban), phenoxyethanol, 2,4,4'-Trichloro-2'-Hydroxy Diphenyl Ether (triclosan); and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include vitamins, minerals, and skin nutrients such as milk, vitamins A, E, and K; vitamin alkyl esters, including vitamin C alkyl esters; magnesium, calcium, copper, zinc and other metallic components; retinoic acid and its derivatives (e.g., cis and trans); retinal; retinol; retinyl esters such as retinyl acetate, retinyl palmitate, and retinyl propionate; vitamin B 3 compounds (such as niacinamide and nicotinic acid), alpha hydroxy acids, beta hydroxy acids, e.g. salicylic acid and derivatives thereof (such as 5-octanoyl salicylic acid, heptyloxy 4 salicylic acid, and 4-methoxy salicylic acid); mixtures thereof and the like.

Skin barrier repair actives are those skin care actives which can help repair and replenish the natural moisture barrier function of the epidermis. Nonlimiting examples of skin barrier repair actives include lipids such as cholesterol, ceramides, sucrose esters and pseudo-ceramides as described in European Patent Specification No. 556,957; ascorbic acid; biotin; biotin esters; phospholipids, mixtures thereof, and the like.

Non-steroidal Cosmetic Soothing Actives can be effective in preventing or treating inflammation of the skin. The soothing active enhances the skin appearance benefits of the present invention, e.g., such agents contribute to a more uniform and acceptable skin tone or color. Nonlimiting examples of cosmetic soothing agents include the following categories: propionic acid derivatives; acetic acid derivatives; fenamic acid derivatives; mixtures thereof and the like. Many of these cosmetic soothing actives are described in U.S. Pat. No. 4,985,459 to Sunshine et al., issued Jan. 15, 1991, incorporated by reference herein in its entirety.

Artificial tanning actives can help in simulating a natural suntan by increasing melanin in the skin or by producing the appearance of increased melanin in the skin. Nonlimiting examples of artificial tanning agents and accelerators include dihydroxyacetaone; tyrosine; tyrosine esters such as ethyl tyrosinate and glucose tyrosinate; mixtures thereof, and the like.

Skin lightening actives can actually decrease the amount of melanin in the skin or provide such an effect by other mechanisms. Nonlimiting examples of skin lightening actives useful herein include aloe extract, alpha-glyceryl-L-ascorbic acid, aminotyrosine, ammonium lactate, glycolic acid, hydroquinone, 4 hydroxyanisole, mixtures thereof, and the like.

Also useful herein are sunscreen actives. A wide variety of sunscreen agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of Cosmetics Science and Technology , all of which are incorporated herein by reference in their entirety. Nonlimiting examples of sunscreens which are useful in the compositions of the present invention are those selected from the group consisting of octyl methoxyl cinnamate (Parsol MCX) and butyl methoxy benzoylmethane (Parsol 1789), 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, mixtures thereof, and the like.

Sebum stimulators can increase the production of sebum by the sebaceous glands. Nonlimiting examples of sebum stimulating actives include bryonolic acid, dehydroetiandrosterone (DHEA), orizanol, mixtures thereof, and the like.

Sebum inhibitors can decrease the production of sebum by the sebaceous glands. Nonlimiting examples of useful sebum inhibiting actives include aluminum hydroxy chloride, corticosteroids, dehydroacetic acid and its salts, dichlorophenyl imidazoldioxolan (available from Elubiol), mixtures thereof, and the like.

Also useful as actives in the present invention are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases, mixtures thereof and the like.

Other useful active ingredients in the present invention are skin tightening agents. Nonlimiting examples of skin tightening agents which are useful in the compositions of the present invention include monomers which can bind a polymer to the skin such as terpolymers of vinylpyrrolidone, (meth)acrylic acid and a hydrophobic monomer comprised of long chain alkyl(meth)acrylates, mixtures thereof, and the like.

Active ingredients in the present invention may also include anti-itch ingredients. Suitable examples of anti-itch ingredients which are useful in the compositions of the present invention include hydrocortisone, methdilizine and trimeprazine, mixtures thereof, and the like.

Nonlimiting examples of hair growth inhibitors which are useful in the compositions of the present invention include 17 beta estradiol, anti angiogenic steroids, curcuma extract, cycloxygenase inhibitors, evening primrose oil, linoleic acid and the like. Suitable 5-alpha reductase inhibitors such as ethynylestradiol and, genistine mixtures thereof, and the like.

Nonlimiting examples of desquamating enzyme enhancers which are useful in the compositions of the present invention include alanine, aspartic acid, N methyl serine, serine, trimethyl glycine, mixtures thereof, and the like.

A nonlimiting example of an anti-glycation agent which is useful in the compositions of the present invention would be Amadorine (available from Barnet Products Distributor), and the like.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below. The following inventive toilet bars may be formulated according to the manufacturing methods described below:

EXAMPLE 1

A useful toilet bar according to a first preferred embodiment of the present invention can be prepared as follows:

| Component | % Weight |
| --- | --- |
| Sodium cocoyl isethionate | 35.5-75% |
| Magnesium cocoyl isethionate | 0.1-35.5% |
| Sodium isethionate | 0.1-10% |
| Magnesium isethionate | 0.1-5% |
| Coco fatty acid | 5-30% |
| Zinc oxide | 0.05-1% |
| Stearic acid | 5-35% |
| Miscellaneous components (note 1) | 1-5% |

Note 1:
optional materials such as one or more of the following (slip enhancement agents, polymeric skin feel agents, skin active agents, plasticizers, fragrance, color, preservatives and the like.

EXAMPLE 2

Several inventive bars were formulated according to Table 1 using the process provided below and compared to comparative bars as described in Table 2 using various criteria including mildness, mush index and wear rates. Concentrations are given in wt. %.

TABLE 1

Inventive Bar Examples A TO D:

| Ingredients | Bar Examples | | | |
| --- | --- | --- | --- | --- |
| | A | B | C | D |
| Sodium cocoyl Isethionate | 65 | 55 | 40 | 60 |
| Magnesium cocoyl Isethionate | 5 | | 10 | 2.5 |
| Calcium cocoyl Isethionate | | 10 | 7 | |
| Ratio of diacyl to monoacyl isethionates | 1:15 or 0.067 | 1:5.5 or 0.18 | 17:40 or 0.43 | 1:24 or 0.042 |
| Sodium Isethionate | 8 | 10 | 8 | 9.5 |
| Calcium Isethionate | | 2 | | |
| Magnesium Isethionate | 2 | | 3 | 2 |
| Sodium Stearate | 1.5 | 1.5 | 1.5 | 4.5 |
| C8-C22 fatty acid soap | 4 | 7 | 13 | 7 |
| Stearic Acid | 7 | 7 | 10 | 7 |
| Coconut Fatty Acid | 2 | 2 | 2 | 2 |
| Water | 5 | 5 | 5 | 5 |
| Preservatives/ Opacifiers | 0.5 | 0.5 | 0.5 | 0.5 |
| Total: | 100 | 100 | 100 | 100 |

Processing Method:

The mono and diacyl isethionates were made as follows: sufficient amounts of coconut fatty acid and isethionate (according to the desired mono/di-valent isethionate ratio) are combined in a vessel with a Lewis acid catalyst and heated to temperatures greater than 230 degrees C. to promote esterification. Once the required conversion is met, a vacuum is applied to the heated vessel so that any excess and unreacted fatty acid may be removed. The material may then be left to solidify or flashcooled into a mixer to begin the toilet bar processing, described below.

The toilet bar was then formulated as follows: first melt the emollients and structurants by heating above 90 C in a z-blade mixer. Then add the anionic surfactants in the mixer and homogenize the mass. Other optional ingredients such as titanium dioxide, brighteners and clays can be added to the mixer at this time. The free water content of the mass is adjusted to about 5-6%. The resulting doughy or flowable liquid mass is then chill roll milled. The milled mass is added in the chip mixer and the rest of the minor ingredients such as color, fragrance and specialty ingredients are added and mixed. The mixed mass is then milled/refined and extruded. The extruded bars are stamped and cartoned/wrapped.

TABLE 2

Comparative Bar or Cleanser Examples E to G

| Ingredients | Bar Examples | | |
|---|---|---|---|
| | E | F | G |
| Sodium cocoyl isethionate | 70 | 25 | 5 |
| Sodium Isethionate | 10 | 1 | 5 |
| Stearic acid | 7 | 26 | 20 |
| Polyethylene glycol | | 19 | |
| Coco Betaine | | 5 | 5 |
| Preservatives/opacifiers | 0.5 | 2 | 2 |
| C8-C22 fatty acid soap | 4 | 13 | 45 |
| Water | 5 | 5 | 5 |
| Fragrance | | 1 | 1 |
| Glycerin | | | 10 |
| Coconut Fatty acid | 2 | 3 | 2 |
| Sodium Stearate | 1.5 | | |
| Total | 100 | 100 | 100 |

Cast Melt Bars.

Flowable and castable inventive compositions can be made using art recognized and other equivalent techniques. Suitable compositions may be made by adding low Krafft point surfactants/emollients/humectants/solvents,etc (preferably KP <30 C) and/or water in a total range of 10-30% by wt., preferably greater than 10%, 12%, 14, and 15% by wt. Very high levels are preferably avoided in order to minimize the mush factor of the toilet bar.

In a preferred embodiment, a mixture of sodium cocoyl isethionate, and magnesium cocoyl isethionate is structured by using some quantity of sodium stearate or 12 hydroxystearic acid in presence of emollients for skin conditioning such as e.g. glycerin, propylene glycol and/or fatty alcohols. These emollients act as solubilizers which are needed to obtain a homogeneous liquid at elevated temperature which on cooling yields a hard bar as determined by its yield stress. Optionally a quantity of cosurfactants with Krafft point preferably less than 30 C can also be used in the formulations.

Method of Making the Bars:

In addition to fragrance, sunflower seed oil, SCl and $MgCl_2$, the remainder of the ingredients are added in a mixer. The mixture is heated to about 90C and mixed slowly to make a homogeneous liquid. SCl and $MgCl_2$ is added slowly and dissolved at about 100 C. Once the mass is homogeneous, the temperature is brought to about 80 C and sunflower seed oil is added slowly with continuous mixing. Fragrance is added to the homogeneous mass preferably at about 70 C to avoid fragrance deterioration. This homogeneous off white liquid is poured into molds. The molds are cooled by suitable cooling techniques or under ambient conditions to obtain solid bars.

EXAMPLE 3

Suitable examples of inventive syndet cleansing bars with varying amounts of magnesium cocoyl isethionate that may be manufactured by the melt cast method discussed above are listed in Table 3:

TABLE 3

| Ingredients | Bar examples | | |
|---|---|---|---|
| | H | I | J |
| Sodium Cocoyl Isethionate | 22.02 | 23.02 | 24.02 |
| Magnesium Cocoyl Isethionate | 3.00 | 2.00 | 1.00 |
| Ratio of diacyl to monoacyl isethionate | 0.14 | 0.087 | 0.042 |
| Stearic acid | 6.58 | 6.58 | 6.58 |
| Sodium Isethionate | 0.45 | 0.45 | 0.45 |
| Magnesium Isethionate | 0.10 | 0.10 | 0.10 |
| Coco Fatty Acid | 0.84 | 0.84 | 0.84 |
| Alpha C14-18 Olefin Sulfonate | 8.00 | 8.00 | 8.00 |
| Sodium Lauryl Ether Sulfate (2 EO) | 8.00 | 8.00 | 8.00 |
| Propylene Glycol | 5.00 | 5.00 | 5.00 |
| Glycerin | 4.00 | 4.00 | 4.00 |
| 12-Hydroxystearic acid | 15.00 | 15.00 | 15.00 |
| Sunflower Seed Oil | 21.01 | 21.01 | 21.01 |
| Fragrance | 1.00 | 1.00 | 1.00 |
| Titanium Dioxide | 1.00 | 1.00 | 1.00 |
| Water | 4.00 | 4.00 | 4.00 |
| Total | 100.00 | 100.00 | 100.00 |

EXAMPLE 4

Other inventive syndet cleansing bars with varying amounts of Magnesium Cocoyl Isethionate that may be manufactured by melt cast route are listed in table 4.

TABLE 4

| Ingredients | Bar examples | | | |
|---|---|---|---|---|
| | K | L | M | N |
| Sodium Cocoyl Isethionate | 24.00 | 23.00 | 22.00 | 21.00 |
| Magnesium Cocoyl Isethionate | 1.00 | 2.00 | 3.00 | 4.00 |
| Ratio of diacyl to monoacyl isethionate | 0.042 | 0.087 | 0.14 | 0.19 |
| Alpha C14-18 Olefin Sulfonate | 8.00 | 8.00 | 8.00 | 8.00 |
| Sodium Isethionate | 0.70 | 0.70 | 0.70 | 0.70 |
| Magnesium Isethionate | 0.30 | 0.30 | 0.30 | 0.30 |
| Sod. Lauryl Ether Sulfate(2EO) | 9.00 | 9.00 | 9.00 | 9.00 |
| Propylene Glycol | 7.00 | 7.00 | 7.00 | 7.00 |
| Glycerin | 7.00 | 7.00 | 7.00 | 7.00 |
| 12-Hydroxy stearic acid | 14.00 | 14.00 | 14.00 | 14.00 |
| Sunflower Seed Oil | 25.00 | 25.00 | 25.00 | 25.00 |
| Water | 4.00 | 4.00 | 4.00 | 4.00 |
| Total | 100.00 | 100.00 | 100.00 | 100.00 |

EXAMPLE 5

Figure 2:
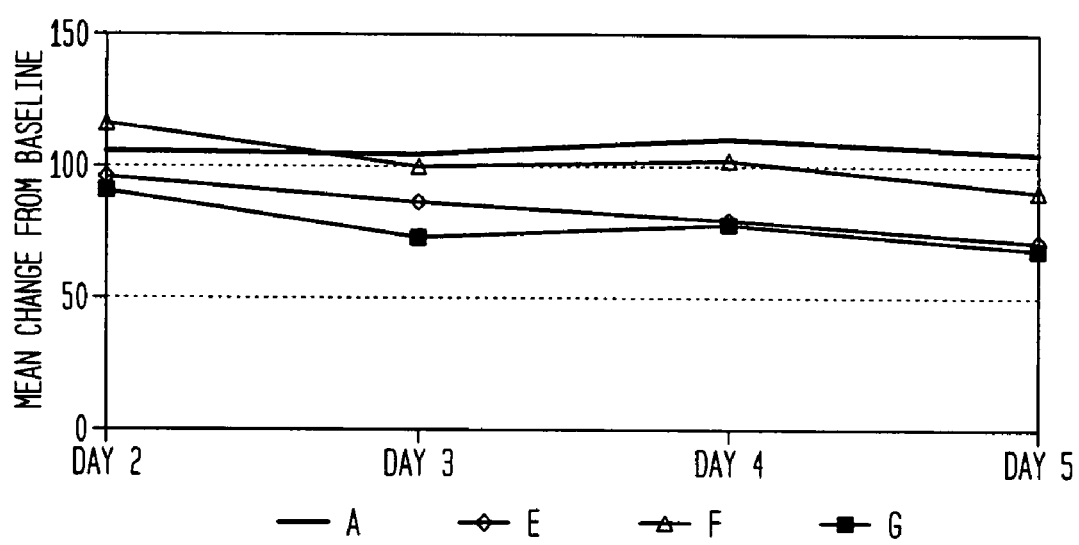
FIG. 2 is a line graph depicting Skicon (conductance) readings (mean change from baseline) of the toilet bars described in table 6.
Figure 3:
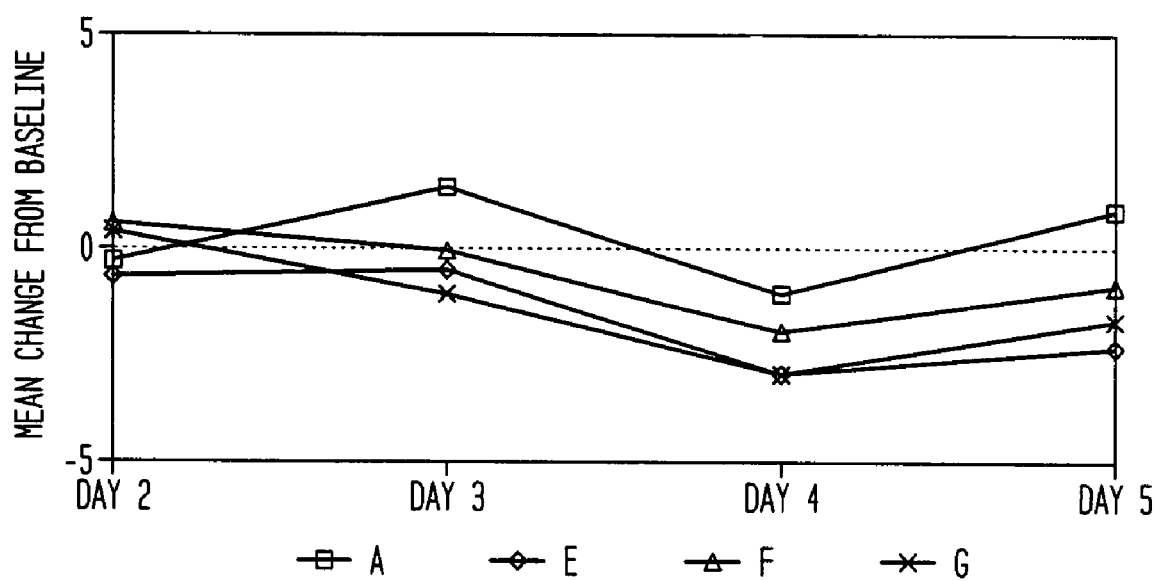
FIG. 3 is a line graph depicting Corneometer (capacitance) readings (mean change from baseline) of the toilet bars described in table 7.

Several bars selected from Tables 1 and 2 were tested to assess their relative mildness by visual dryness and erythema assessment in combination with non-invasive instrumental assessments during a five-day treatment period in a randomized, double-blind study according to FCAT methodology (as described below). The mildness data of inventive bars are compared to the comparative bars in FIGS. 1-3 illustrating the data in tables 5 to 7 respectively.

The data in tables 5 to 7 are the visual scores obtained at baseline and nine post-treatment time points, and instrument readings obtained at baseline and on Days 2 through 5 (for the Skicon conductance and Corneometer capacitance readings) and on Day 5 for the TEWL readings. The data used in the statistical analysis were the differences from baseline for each bar sample.

Both within-treatment statistical analysis and between-treatment statistical analysis were performed. For the within-treatment case, the performance of each bar at each time point compared to its respective baseline was evaluated using the paired t-test. Hypothesis ($H_o$: $\bar{d}=0$) testing was conducted at the $p=0.05$ level. For the between-treatment case, analysis of variance (ANOVA) techniques were used to compare the extent of change from baseline among the bars with subjects and arms (nested within subjects) as random effects and sites and treatments as fixed effects. A term for the interaction of sites and treatments was also included in the model. In the event of significant test article effects, the least square means analysis was performed to make comparisons between selected pairs with all hypothesis testing being performed at the $p=0.05$ level.

TABLE 5

Mean Change from Baseline - DAY 5 (FINAL) TEWL Readings for bar samples A and E-G.

| A | E | F | G |
|---|---|---|---|
| 2.68 | 3.72 | 3.14 | 4.08 |

ANOVA p-value < 0.0001

TABLE 6

Mean Changes from Baseline - Skicon Readings - Day 2 to Day 5 for bar samples A and E-G.

| Sample | Day 2 | Day 3 | Day 4 | Day 5 |
|---|---|---|---|---|
| A | 105.27 | 104.01 | 109.26 | 103.99 |
| E | 106.13 | 93.58 | 98.58 | 81.94 |
| F | 115.57 | 100.33 | 101.76 | 90.41 |
| G | 90.56 | 82.16 | 86.80 | 74.56 |
| ANOVA p-value | <0.0001 | <0.0001 | $0.2720^2$ | <0.0001 |

TABLE 7

Mean Changes from Baseline - Corneometer Readings, Day 2 to Day 5 for bar samples A and E-G.

| Sample | Day 2 | Day 3 | Day 4 | Day 5 |
|---|---|---|---|---|
| A | −0.24 | 1.46 | −1.01 | 0.95 |
| E | −0.63 | −0.48 | −2.87 | −2.24 |
| F | 0.67 | 0.00 | −1.86 | −0.80 |
| G | 0.47 | 0.31 | −1.89 | −1.17 |
| ANOVA p-value | <0.0001 | <0.0001 | <0.0001 | <0.0001 |

EXAMPLE 6

The mush factor was determined for several bars selected from Tables 1 and 2 using the method described below. The results are summarized in Table 8 and show that the mild inventive bar tends to have mush attributes closer to the traditional soap bar than the comparative and higher mushing mild acyl isethionate bars.

TABLE 8

Product mush index

| | Sample | | | |
|---|---|---|---|---|
| | A | E* | F | G |
| g mush/50 cm$^2$ | 6.2 | 10.1 | 10.2 | 8.2 |
| Mush Factor | 0.61 | 1.00 | 1.01 | 0.81 |

*Control Bar

EXAMPLE 7

The wear rate was determined for several bars selected from Tables 1 and 2 using the method described below. The results are summarized in Table 10 and show that the mild inventive bar tends to have wear rate attributes closer to the traditional soap bar than the comparative mild, acyl isethionate bar.

TABLE 10

Product wear rate

| | Sample | | | |
|---|---|---|---|---|
| | A | E | F | G |
| % Bar Loss | 8.9 | 10.5 | 9.6 | 9.4 |

EXAMPLE 8

Several inventive bars according to a second preferred embodiment were formulated according to Table 11 using the process provided above and compared to comparative bars using various criteria including hardness, lather, wear rate, and Zein value (i.e. mildness). Concentrations are given in wt. %.

TABLE 11

| | Examples | | | | | | |
|---|---|---|---|---|---|---|---|
| Components | 1 comp | 2 comp | 3 comp | 4 comp | 5 comp | 6 comp | 7 comp |
| NaCl* | 50 | — | — | — | 25 | 25 | — |
| CaCl* | — | 50 | — | — | — | 25 | 30 |
| MgCl* | — | — | 50 | — | 25 | — | 20 |
| ZnCl* | — | — | — | 50 | — | — | — |
| Ca:Mg diacyl isethionate WT % ratio | — | — | — | — | — | — | 3:2 or 1.5 |
| Fatty Acids | 24 | 24 | 24 | 24 | 24 | 24 | 24 |
| Soap** | 10 | 10 | 10 | 10 | 10 | 10 | 10 |
| Salt*** | 5 | 5 | 5 | 5 | 5 | 5 | 5 |
| Misc. (5) | 5 | 5 | 5 | 5 | 5 | 5 | 5 |
| Water | 6 | 6 | 6 | 6 | 6 | 6 | 6 |
| Hardness, kPa, 40 C., (1) | 180 | 110 | 145 | 150 | 160 | 135 | 100 |
| Lather, ml (2) | 120 | 50 | 140 | 135 | 100 | 70 | 70 |
| Wear Rate, g/w (3) | 2.0 | 1.7 | 2.5 | 2.5 | 2.1 | 2.2 | 2.4 |
| ****Zein, % (4) | 2.5 | 0.5 | 2.0 | 2.1 | 2.3 | 1.8 | 1.4 |

| | 8 inv | 9 inv | 10 inv | 11 inv |
|---|---|---|---|---|
| NaCl* | — | — | — | 15 |
| CaCl* | 20 | 15 | 10 | 15 |
| MgCl* | 30 | 35 | 40 | 20 |
| ZnCl* | — | — | — | — |

TABLE 11-continued

| | | | | |
|---|---|---|---|---|
| Ca:Mg diacyl isethionate ratio | 2:3 or 0.67 | 15:35 or 0.43 | 1:4 or 0.25 | 3:4 or 0.75 |
| Fatty Acids | 24 | 24 | 24 | 24 |
| Soap** | 10 | 10 | 10 | 10 |
| Salt*** | 5 | 5 | 5 | 5 |
| Misc. (5) | 5 | 5 | 5 | 5 |
| Water | 6 | 6 | 5.5 | 5.5 |
| Hardness, kPa (1) | 125 | 140 | 140 | 160 |
| Lather, ml 2) | 110 | 125 | 140 | 120 |
| Wear Rate, g/w (3) | 2.1 | 2.0 | 2.3 | 2.2 |
| ****Zein, % (4) | 1.5 | 1.7 | 1.9 | 1.75 |

*MeCI—metal cocoyl isethionate (Me=Na, Ca, Mg, Zn)
**sodium, potassium or magnesium soap
***sodium-, magnesium-, calcium-, zinc- isethionate
****to be perceptible to the consumer, the zein score should be ca. at least 30% less than a control bar.
(1) consumer acceptable range is 120-240 kpa at 40 C.
(2) consumer acceptability criteria is >100 mls
(3) consumer acceptability criteria is 1.8-2.3 g/w
(4) consumer acceptability criteria is <=2.5
(5) Misc. includes colorants, fragrance, preservatives, etc.

According to a second embodiment of the invention, examples 2-4 demonstrate that bars comprising acyl isethionates with a single type divalent counter-ion are not acceptable according to at least two out of four main consumer requirements: hardness, lather, wear rate, and zein score. Similarly examples 5-7 demonstrate that bars comprising acyl isethionates with a ratio of counter-ions (monovalent and divalent) outside of the invention are not acceptable according to at least one out of the four consumer requirements: hardness, lather, wear rate, zein score. Finally examples 8-11 demonstrate that the ratio of calcium to magnesium diacyl isethionates should be within the 0.25 to 0.80 range in order to largely satisfy all four stated consumer requirements.

Description of Test Methods:

Test Methods a) Mush Test

Shave the bar to the dimensions of 7 cm×4 cm×2 cm and carve a line halfway down the center of the bar (at the 3.5 cm mark). Measure the weight of the bar. Suspend half of the bar (3.5 cm) in deionized water for 2 hours at a temperature of 25 C. After this time, lift up the bar and remove excess water by suspending the bar for 30 seconds, then weigh the bar. This is the weight of the bar, the mush, and the absorbed water. After weighing, lightly scrape off the mush from the bar, being careful not to scrape off excess bar material that is not mush. Discard the mush and let the bar dry for 12 hours. Weigh the final dry bar and the difference of the initial dry bar and the final dry bar, calculated for the 50 cm² bar surface area, is the amount of mush (grams). The difference in weight of the soaked bar and the initial dry bar is the amount of water absorbed. The Mush Factor is defined as the ratio of the mush/50 cm² of a given bar to a control mild isethionate bar mush/50 cm² or in the present case, formula E provided above. For example, the mush of the inventive bar (formula A) is 6.2 g mush/50 cm², and the mush of formula E is 10.1 g mush/50 cm² to provide a Mush Factor of 0.61.

b) Wear Rate Method

Weigh the bar to be tested. Set up an 8 liter bucket with continuous water running through it at 40.5 C. Immerse the bar and rotate it in the hands 20 times. Repeat. Immerse the bar again to remove adhering lather, and let dry in the air at 25 C and approx. 50% RH in a dish. Repeat every two hours over an 8 hour span. Let dry for 12 hours at 25 C and approx. 50% RH in a dish and repeat for another 8 hour span.

Add 10 g of deionized water to the dish between immersions and while the bar is resting in the dish, (this should be additive over the 8-hour span—meaning that after the first 2 hours 10 g water are added to the dish; after 4 hours, add 10 grams more, totaling 20 grams water in the dish. After 6 hours, add 10 grams more, totaling 30 g water in the dish, and so on for the 8 hour period, then let dry for 12 hours. The weight of the bar after 12 hours is recorded and the wear rate is the percent weight loss of the bar.

An alternative Wear Rate Method applied to example 8 is as follows:

1. Record the weight of each bar prior to being washed.
2. Adjust the faucet water to 105° F. (40° C.) and keep it running into a bucket
3. Immerse the bar and hands into the bucket.
4. Remove the bar from the water and rotate twenty (20) half turns.
5. Repeat steps (3) and (4).
6. Immerse the bar for a third time then place into a soap dish.
7. Add 7.5 ml of water to the soap dish.
8. Repeat the wash procedure, steps (2) through (6), three additional times during the first day. The washes should be spaced evenly throughout the work day.
9. After the last wash of the day, add 7.5 ml of water to the soap dish and let the bar sit overnight.
10. The following morning repeat the wash procedure, steps (2) through (6), then place the bar sideways on a drying rack.
11. Allow the bar to sit for 24 hours then weigh the bar to the nearest 0.01 gm.

Calculation:

Wear Rate (gm/wash)=(Initial weight−Final weight)/Number of washes c) Krafft Point Determination Make up a 10% by wt. solution of surfactant or other sample in water. If needed, heat the system to dissolve the sample completely. Transfer the clear solution to a glass test tube. Place the test tube in a beaker equipped with a stirrer and filled with sufficient water to evenly cool the surfactant or sample solution. The solution should be cooled with continuous stirring and the temperature should be continuously recorded. Note the temperature when the crystallization process begins such that the solution becomes turbid. This temperature is taken as the Krafft point. If the crystallization temperature is below room temperature, add ice to the beaker to cool the test tube below room temperature to measure the subambient Krafft point.

D) Method for Calculation of Yield Stress with Cheese Cutter Device

An approximate value for yield stress can be determined by the cheese cutter method. The principle of the measurement is that a wire penetrating into a material with a constant force will come to rest when the force on the wire due to stress balances the weight. The force balance is:

Weight driving wire=force on wire due to material stress $m\,g = K\,ys\,lD$

Where:

m=mass driving wire (actual mass used in calculation is the mass placed on the device plus the weight of the arm which adds to the extra weight on the sample)
g=gravitational constant, 9.8 m/sec$^2$
ys=yield stress
l=length of penetration of wire into soap after 1 minute (mm)
D=diameter of wire (mm)
K=a geometrical constant The final equation is:

$$ys = (3/8) m\, g/(l\, D)$$

Procedure:

Cut a square of soap and position on the yield stress device. Place a mass on the yield stress device while holding the arm. 400 g is an appropriate mass, although less might be needed for a very soft material. Gently lower the arm so the wire just touches the soap and let the arm go. Stop the vertical motion of the arm after one minute, and push the soap through the wire horizontally to cut a wedge out of the sample. Take the mass off the device and then measure the length of the cut in the sample. The wire would continue to cut the soap at a slow rate, but the length of the cut made by the wire in one minute is taken as the final value. Measure the temperature of the soap while the test proceeds.

Sample Calculation:

A 400 gram weight is used on the yield stress device and a 22 mm slice is measured where the wire has cut the soap after 1 minute. Assuming the diameter of the wire is 0.6 mm, the approximate yield stress is $$\frac{(3/8)\,(400+56)\,[g]\,9.8\,[m/sec^2]\,10^{-3}\,[kg/g]}{22\,[mm]\,0.6\,[mm]\,10^{-6}\,[m^2/mm^2]} = 1.3105\ \text{Pa or 130 kPa}$$

If a counterbalance is used on the wire contacting the bar, the value of 56 is subtracted from "m" in the formula above. Optionally an Instron testing device (supplied by Instron Co., Boston, Mass.) may be used instead of a weight to apply stress to the wire contacting the bar.

e) Mildness Test:

i) The mildness of selected inventive toilet bars was assessed by the Forearm Controlled Application Test (FCAT) Clinical Test Methodology as follows:

This controlled washing test is similar to that described by Ertel et al (A forearm controlled application technique for estimating the relative mildness of personal cleansing products, J. Soc. Cosmet. Chem., 46, 67 (1995)).

Subjects report to the testing facility for the conditioning phase of the study, which consists of using an assigned marketed personal washing cleanser for general use at home, up to four days prior to start of the product application phase. On Day 1 of the product application phase, a visual assessment is made to determine subject qualification. Subjects must have dryness scores >1.0 and erythema scores >0.5, and be free of cuts and abrasions on or near the test sites to be included in the product application phase. Subjects who qualify to enter the product application phase will then be instructed to discontinue the use of the conditioning product and any other skin care products on their inner forearms, with the exception of the skin cleansing test formulations that are applied during the wash sessions.

Qualified subjects will then have four 3.0-cm diameter (round) evaluation sites marked on each of the forearms using a skin safe pen (a total of eight sites). Visual evaluations for erythema and dryness will be conducted immediately prior to the first wash in each session and again in the afternoon of the final day (Day 5).

Washing Procedure for Bar Products

1. Both arms are washed simultaneously. Test sites are treated in a sequential manner starting with the site closest to the flex area, ending with the site proximal to the wrist.

2. The sites closest to the flex area of the inner forearm of both the right and left arm are moistened with warm water (about 35 C.).

3. A moistened Masslinn towel is rubbed in a circular motion on a wetted test bar for approximately 6 seconds by study personnel which will result in 0.2-0.5 g of product to be dispensed.

4. The site is washed with the designated product for 10 seconds followed by a 90-second lather retention phase.

5. The above procedure (1-4) is then repeated for each of the test sites. Sites are then rinsed (e.g. using a temperature of 35 C) for fifteen seconds and patted dry.

6. Upon completion the entire procedure is repeated (two washes/session).

Evaluation Methods

Baseline visual assessments are made prior to the start of the product application phase, and immediately before each wash session thereafter, to evaluate dryness and erythema. The final visual evaluation is conducted on the afternoon of the final day.

The 0-6 grading scale shown in Table B is used to assess the test sites for dryness and erythema. To maintain the evaluator's blindness to product assignment, visual assessments are conducted in a separate area away from the product application area.

TABLE B

Erythema and Dryness grading scale.

| Grade | Erythema | Dryness |
|---|---|---|
| 0 | None | None |
| 1.0 | Barely perceptible | Patches of slight powderiness and redness occasional patches of small scales may be seen. Distribution generalized. |
| 2.0 | Slight redness | Generalized slight powderiness. Early cracking or occasional small lifting scales may be present |
| 3.0 | Moderate redness | Generalized moderate powderiness and/or heavy cracking and lifting scales. |
| 4.0 | Heavy or substantial | Generalized heavy powderiness and/or redness heavy cracking and lifting scales |
| 5.0 | Extreme redness | Generalized high cracking and lifting scales. Powderiness may be present but not prominent. May see bleeding cracks. |
| 6.0 | Severe redness | Generalized severe cracking. Bleeding cracks. Bleeding cracks may be present. Scales large, may be beginning to disappear. |

Instrumental readings are taken on the first (baseline) and final day of the study. Mildness of test product is calculated as 1/(mean change in dryness at end of the study). In addition to visual evaluation, instrumental assessments of the treated sites are conducted using an evaporimeter and skin conductance meter as described in the reference above.

Instrumental Assessment

All instrumental evaluations are taken following a 30-minute acclimation period. The indoor humidity and temperature data are recorded and included in the final report. Instrumental measurements may be taken at some or all of the following time points: 0, 1, 2, 4, 6, 8 and 24 hours after product application. Instruments that may be used with this protocol include: The Derma Lab Model #CR 200001-140, ServoMed Evaporimeter with EP1 or EP2 probe, Corneometer CM820, the Skicon Skin Hygrometer with the MT-8C probe, and the Moisture Checker. The room temperature is maintained at 20° to 25° C. and 30% to 40% Relative Humidity. Moisturization is defined as mean change from baseline of visual dryness or skin hydration.

Transepidermal Water Loss Test (TEWL)

The Derma Lab Model #CR 200001-140 was used to quantify the rates of transepidermal water loss following the procedures similar to those outlined by Murahata et al ("The use of transepidermal water loss to measure and predict the irritation response to surfactants" Int. J. Cos. Science 8, 225 (1986)). TEWL provides a quantitative measure of the integrity of the stratum corneum barrier function and the relative effect of cleansers.

The operating principle of the instrument is based on Fick's law where $$(1/A)(dm/dt)=-D(dp/dx)$$

where
A=area of the surface ($m^2$)
m=weight of transported water (g)
t=time (hr)
D=constant, 0.0877 g-1 h-1 (mm Hg)-1 related to the diffusion coefficient of water
p=partial pressure of water vapor in air (mm Hg)
x=distance of the sensor from the skin surface (m)

The evaporation rate, dm/dt, is proportional to the partial pressure gradient, dp/dx. The evaporation rate can be determined by measuring the partial pressures at two points whose distance above the skin is different and known, and where these points are within a range of 15-20 mm above the skin surface. The general clinical requirements are as follows:
1. All panelists are equilibrated for a minimum of fifteen minutes before measurements in a test room in which the temperature and relative humidity are controlled.
2. The test sites are measured or marked in such a way that pre and post treatment measurements can be taken at approximately the same place on the skin.
3. The probe is applied in such a way that the sensors are perpendicular to the test site, using a minimum of pressure.

Probe Calibration is achieved with a calibration set (No. 2110) which is supplied with the instrument. The kit must be housed in a thermo-insulated box to ensure an even temperature distribution around the instrument probe and calibration flask.

The three salt solution used for calibration are LiCl, Mg[NO3]2, and K2SO4. Pre-weighed amounts of salt at high purity are supplied with the kit instrument. The solution concentrations are such that the three solutions provide a RH of Ã11.2%, Ã54.2%, and Ã97% respectively at 21° C.

General use of the instrument is as follows:
1. For normal studies, instrument readings are taken with the selector switch set for 1-100 g/m2 h range
2. The protective cap is removed from the probe and the measuring head is placed so that the Teflon capsule is applied perpendicularly to the evaluation site ensuring that a minimum pressure is applied from the probe head. To minimize deviations of the zero point, the probe head should be held by the attached rubber-insulating stopper.
3. Subject equilibration time prior to prior to evaluation is 15 minutes in a temperature/humidity controlled room.
4. The probe is allowed to stabilize at the test site for a minimum of 30 seconds before data acquisition. When air drafts exist and barrier damage is high it is recommended to increase the stabilization time.
5. Data is acquired during the 15 seconds period following the stabilization time.

Skin Hydration Test

The Corneometer CM802PC (Courage & Khazaha, Kohl, Germany) is a device widely used in the cosmetic industry. It allows high frequency, alternating voltage electrical measurements of skin capacitance to be safely made via an electrode applied to the skin surface. The parameters measured have been found to vary with skin hydration. However, they may also vary with many other factors such as skin temperature, sweat gland activity, and the composition of any applied product. The Corneometer can only give directional changes in the water content of the upper stratum corneum under favorable circumstances but even here the quantitative interpretations may prove misleading.

A widely used alternative is the Skicon Skin conductance Meter (I.B.S. Co Ltd. Shizuoka-ken, Japan).

Panelist Requirements for either instrument are as follows:
1. Subjects should equilibrate to room conditions, which are maintained at a fixed temperature and relative humidity for a minimum of 15 minutes with their arms exposed. Air currents should be minimized.
2. Physical and psychological distractions should be minimized, e.g., talking and moving around.
3. Consumption during at least 1 hour before measurement of hot beverages or of any products containing caffeine should be avoided.
4. Panelists should avoid smoking for at least 30 minutes prior to measurements.

Operating Procedure
1. The probe should be lightly applied so as to cause minimum depression of the skin surface by the outer casing. The measuring surface is spring-loaded and thus the probe must be applied with sufficient pressure that the black cylinder disappears completely inside the outer casing.
2. The probe should be held perpendicular to the skin surface.
3. The operator should avoid contacting hairs on the measure site with the probe.
4. The probe should remain in contact with the skin until the instrument's signal beeper sounds (about 1 second) and then be removed. Subsequent measurements can be made immediately provided the probe surface is known to be clean.
5. A minimum of 3 individual measurements should be taken at separate points on the test area and averaged to represent the mean hydration of the site.
6. A dry paper tissue should be used to clean the probe between readings.

f) Moisturizer Deposition Test:

The deposition of optional moisturizers (i.e. skin conditioning agents) formulated in a sample bar may be quantified using the following procedure. Precondition the subject's skin (arms/legs) with a non-moisturizer containing product for up to 2 days prior to testing. A baseline extraction is performed to estimate level of moisturizer (e.g.: fatty acids) present on the skin prior to product application. Controlled single application of product to skin (arms or legs) is made. For wash, bar is rubbed on skin for 30 sec. and the lather left on for 90 sec., rinsed for 30 sec. (e.g. using a temperature of 35 C) then gently pat dry. Following this, the site is extracted using a suitable solvent (IPA)/methanol 1:1). The extraction is performed as follows: A glass cup (3 cm diameter) is placed on the skin. 3 mls of solvent is placed into this and gently stirred with a glass rod for 2 minutes. The solvent is removed with a pipette. This step is repeated with a fresh 3 mls of solvent, to collect a total of 6. mls extract. The extracts are analyzed for stearic acid/palmitic acid content using either LC/MS or GC/MS, or the like.

g) Skin Abrasiveness Test

When optional exfoliants are present in the sample bar, the perceived skin abrasiveness of the bar may be determined using the following procedure. Skin abrasiveness is defined as consumer rated response of abrasivity on a 0-9 scale (0 means no abrasion, 10 is abrasivity caused by a pouf (i.e. a showering implement composed of thin plastic filaments, see also e.g. U.S. Pat. No. 5,650,384 to Gordon et al.).

This test is performed with 50 untrained consumers. They are asked to rate the abrasiveness of the test product on a 0-9 point scale. The data is normalized based on their response to a bar with no exfoliants which is assigned a value of zero and a pouf that is assigned a value of 9. The test products are applied to the flex area of the forearm by wetting the bar and rubbing back and forth 10-15 times.

h) pH Test Method

The pH of a sample bar may be tested with the following procedure. Form an aqueous slurry by blending 10 grams of the bar formula with 90 g of water to create a 10% slurry. The pH of the slurry is then measured at 25 C using a conventional pH meter.

i) Zein Test Method

The inventive toilet bar preferably has a zein solubility of under about 50, 40, 30, and most preferably under about 25 using a first zein solubility method set forth below. The lower the zein score, the milder the product is considered to be. This method involves measuring the solubility of zein (corn protein) in cleansing base solutions as follows:

0.3 g of cleansing base and 29.7 g of water at room temperature (25 C) are mixed thoroughly. To this is added 1.5 g of zein, and mixed for 1 hour. The mixture is then centrifuged for 30 minutes at 3000 rpm. After centrifugation, the pellet is extracted, washed with water, and dried in a vacuum oven for 24 hours until substantially all the water has evaporated. The weight of the dried pellet is measured and percent zein solubilized is calculated using the following equation:

% Zein solubilized=100(1−weight of dried pellet/1.5).

The % Zein is further described in the following references: E. Gotte, Skin compatibility of tensides measured by their capacity for dissolving zein protein, Proc. IV International Congress of Surface Active Substances, Brussels, 1964, pp 83-90.

An alternative second Zein Test Method applied to example 8 was used as follows:

Day 1:
 1. Using a grater or spatula, shave bar sample into ribbons
 2. Make a 5% by weight slurry* using 3 g. bar sample, 57 g. DI water
 3. Stir samples for 24 hours at 600 rpm.

Day 2:
 1. Measure and record pH of samples
 2. Add 1 g of Zein protein to 20 mL of slurry in separate container—run in duplicate
 3. Stir at 600 rpm for 20 minutes, then let sit for 24 hours Day 3:
 1. Measure pH of Zein samples
 2. Remove supernatant of each sample, transfer to a centrifuge tube
 3. Transfer some of original slurry into centrifuge tubes as well
 4. Centrifuge all samples for 30-60 minutes at 3000-3500 rpm, repeat if necessary until all solutions can be filtered with a 0.45 micron pore syringe filter
 5. Filter all solutions with a 0.45 micron syringe filter
 6. Dilute samples and background samples (original slurry) by 25× with 2% SDS (e.g. 0.200 g. sample solution+4.8 g. 2% SDS)—record weights to calculate dilution factor
 7. Using a microplate, fill 4 wells per sample with 200 μL of sample, also filling 4 wells with each background sample, as well as 4 wells with 2% SDS
 8. Measure UV-vis absorbance at 278 nm, average the 4 readings of each
 9. The "true Zein reading" (after corrections for the absorbance of SDS and the background absorbance of the original slurries) is then derived using the calibration curve of UV absorbance vs. known concentration of zein in SDS solutions.

For comparison, a typical Zein value for a Dove® bar is ca. 2.5wt. % j) Patch Testing

A 48 hr continuous or 14 day cumulative insult patch test may be used to assess product mildness: In the 48 hr patch test 5-15% solution/slurry of the product is applied onto the upper arm/back of the subject using a standard cotton pad. Irritation response is recorded for up to 24 hrs after removal of the patch. In the 14 day cumulative test a 5-15% solution/slurry of the product is applied repeatedly every 24 hrs for 14 days. Irritation response is recorded for up to 24 hrs after removal of patch.

Mildness of test product is evaluated as 1/(mean erythema at 24 hr after final patch removal).

k) Extensional Stress Test Method

Extensional force at constant deformation rate is measured with e.g. an Instron Tensile Tester model 3211 equipped with a 500 newton compression load cell and equipped with a penetrometer having a probe ending with a sharp edged disk with a diameter of preferably 2, 4 or 11 mm. During measurement, the probe is lowered into the sample at constant speed and the force is continuously recorded. Extensional rate, E, is calculated from the velocity of the probe and the diameter of the disk using the formula below:

$$E=4V/d$$

Where V is the velocity of the probe in mm/sec and d is the diameter of the probe in mm.

The extensional stress, $\Sigma$, is calculated from the measured force and the diameter of the disc at 35 degrees C. using the following formula:

$$\Sigma = \frac{3F}{\pi d^2}$$

Where F is the force applied to the probe in Kpa and d is the probe diameter in mm.

l) Lather Measurement Procedure

The volume of lather which is generated and collected from a given bar formulation under a strict regimen of washing is measured using the inverted funnel method as follows:

The measuring funnel is constructed by fitting a 10½ inch diameter plastic funnel to a graduated cylinder which has had the bottom cleanly removed. Preferably the graduated cylinder volume should be 150 cc or greater. The fit between the funnel and the graduated cylinder should be snug and secure.

Procedure

Before evaluations proceed, place the measuring funnel into one of the sinks and fill the sink with water until the 0 cc mark is reached on the graduated cylinder.

Run the faucet in the second sink and set the temperature to 95° F. (35° C.). Holding the bar between both hands under running water, rotate the bar for ten (10) half turns.

Remove hands and bar from under the running water.
Rotate the bar fifteen (15) half turns.
Lay the bar aside.
Work up lather for ten (10) seconds.
Place funnel over hands.
Lower hands and funnel into the first sink.
Once hands are fully immersed, slide out from under funnel.
Lower the funnel to the bottom of the sink.
Read the lather volume.
Remove the funnel with lather from the first sink and rinse in the second sink.

The test is performed on 2 bars of the same formulation, same batch etc. and the volume is reported as an average of the 2 assessments.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A toilet bar, comprising:
   (a) 1 to about 30% by wt. of a fatty acid soap;
   (b) about 15 to 75% by wt. of a blend of C8-C18 diacyl and monoacyl isethionates; wherein the ratio of the diacyl to monoacyl isethionates is in the range of about 0.04 to 0.5; and (C) about 10 to 40% by wt. of C8-C18 total fatty acids.

2. The toilet bar of claim 1 wherein the bar has a yield stress value from about 100 Kpa to 650 KPa at 25° C. and 50% RH.

3. The toilet bar of claim 1 further comprising about 0.1 to 15% by wt. of a blend of alkali and alkaline earth metal isethionate salts wherein the blend ratio of the alkaline earth to alkali metal isethionates is in the range of about 0.04 to 0.5.

4. The toilet bar of claim 1 wherein the diacyl isethionate(s) counterion is/are selected from magnesium, calcium or a blend thereof and the monoacyl isethionate(s) counterion is/are selected from sodium, potassium or a blend thereof.

5. The toilet bar of claim 1 which contains 1 to about 20% by wt. of fatty acid soap.

6. The toilet bar of claim 1 which contains about 25 to 74% by wt. of C8-18 monoacyl isethionates and about 0.1 to 35% by wt. of C8-C18 diacyl isethionates provided that the total mono and diacyl isethionates cannot exceed 75% by wt. of the total bar.

7. The toilet bar of claim 1 wherein at least about 60% by wt. of the diacyl isethionate(s) present is magnesium cocoyl isethionate and at least about 60% by wt. of the monoacyl isethionate(s) present is sodium cocoyl isethionate.

8. The toilet bar of claim 1 which contains about 35 to 55% by wt. of the blend of C8-C18 alkali and alkaline earth metal acyl isethionates.

9. The toilet bar of claim 1 which contains about 0.1 to 10% by wt. of sodium isethionate and about 0.1 to 10% by wt. of magnesium isethionate.

10. The toilet bar of claim 1 wherein the fatty acid soaps include a blend of C6 to C22 soaps.

11. The toilet bar of claim 1 further comprising at least one non-soap anionic surfactant(s) selected from C8 to C22 alkyl sulfate(s), C8 to C22 alkyl sulfosuccinate(s), C8 to C22 alkyl sulfonate(s); C8 to C22 fatty acid ester sulfonate(s), derivatives, and blend(s) thereof in a range of 0.1 to 15% by wt. as the total amount of non-soap anionic surfactant(s) excluding isethionates.

12. The toilet bar of claim 1 further comprising at least about 0.05% by wt. of one or more compounds selected from zinc oxide, zirconium oxide, zinc chloride, or zinc cocoate.

13. The toilet bar of claim 1 wherein the amount of free water is less than about 15% by wt.

14. A toilet bar, comprising:
   (a) 1 to about 30% by wt. of a fatty acid soap;
   (b) about 20 to 70% by wt. of a blend of calcium and magnesium C8-C18 diacyl isethionates, wherein the ratio of calcium to magnesium diacyl isethionates is in the range of about 0.25 to 0.8; and (C) about 10 to 40% by wt. of C8-C18 total fatty acids.

15. The toilet bar of claim 14 wherein the bar has a yield stress value from about 120 KPa to 240 KPa at 40° C. and 50% RH.

16. The toilet bar of claim 14 further comprising one or more C8-C18 monoacyl isethionates; wherein the maximum ratio of mono to diacyl isethionates is about 0.5.

17. The toilet bar of claim 14 wherein the ratio of calcium to magnesium is in the range of about 0.4 and 0.8.

18. The toilet bar of claim 14 further comprising about 0.1 to 15% by wt. of a blend of alkali and alkaline earth metal isethionate salts wherein the blend ratio of the alkaline earth to alkali metal isethionates is in the range of about −0.04 to 0.5.

19. The toilet bar of claim 14 which contains about 0.1 to 10% by wt. of sodium isethionate and about 0.1 to 10% by wt. of magnesium isethionate.

* * * * *